United States Patent
Briggs et al.

(10) Patent No.: US 6,586,657 B2
(45) Date of Patent: Jul. 1, 2003

(54) METHODS FOR ENHANCING DISEASE RESISTANCE IN PLANTS

(75) Inventors: Steven Briggs, Del Mar, CA (US); Carl R. Simmons, Des Moines, IA (US); John T. Tossberg, Des Moines, IA (US)

(73) Assignee: Pioneer Hi-Bred International, Inc., Des Moines, IA (US)

(*) Notice: Subject to any disclaimer, the term of this patent is extended or adjusted under 35 U.S.C. 154(b) by 0 days.

(21) Appl. No.: 09/915,674

(22) Filed: Jul. 26, 2001

(65) Prior Publication Data

US 2002/0029392 A1 Mar. 7, 2002

Related U.S. Application Data

(62) Division of application No. 09/256,898, filed on Feb. 24, 1999, now Pat. No. 6,476,292.
(60) Provisional application No. 60/092,464, filed on Jul. 11, 1998, and provisional application No. 60/076,151, filed on Feb. 26, 1998.

(51) Int. Cl.$^7$ .......................... A01H 5/00; C12N 15/09; C12N 15/31; C12N 15/82; C12N 15/70
(52) U.S. Cl. .......................... 800/279; 800/278; 800/288; 800/320; 800/320.1; 435/320.1; 435/419; 435/468; 435/430; 536/23.7; 536/24.1
(58) Field of Search .................... 800/278, 279, 800/288, 320, 320.1; 435/320.1, 419, 468, 430; 536/23.7, 24.1

(56) References Cited

U.S. PATENT DOCUMENTS

| 5,981,843 A | 11/1999 | Chappell et al. | |
|---|---|---|---|
| 6,127,607 A | * 10/2000 | Ausubel et al. ............. | 800/301 |

FOREIGN PATENT DOCUMENTS

| WO | WO 91/15585 A1 | 10/1991 |
|---|---|---|
| WO | WO 94/01546 A1 | 1/1994 |
| WO | WO 95/28423 A1 | 10/1995 |
| WO | WO 95/28478 A1 | 10/1995 |
| WO | WO 95/31564 A2 | 11/1995 |
| WO | WO 96/22375 A2 | 7/1996 |
| WO | WO 96/30530 A1 | 10/1996 |
| WO | WO 96/35790 A1 | 11/1996 |
| WO | WO 96/36697 A1 | 11/1996 |
| WO | WO 97/47756 A1 | 12/1997 |

OTHER PUBLICATIONS

Whalen et al, "Avirulence Gene avrRxv from *Xanthomonas capestris* pv. vesicatoria Specifies Resistance on Tomato Line Hawaii 7998", 1993, Molecular Plant Microbe Interaction, vol. 6 (5), pp. 616–627.*

Alvarez, M., et al., "Reactive Oxygen Intermediates Mediate a Systemic Signal Network in the Establishment of Plant Immunity," *Cell*, Mar. 20, 1998, pp. 773–784, vol. 92, Cell Press.

Bennetzen, J. and J. Jones, "Approaches and Progress in the Molecular Cloning of Plant Disease Resistance Genes," *Genetic Engineering*, 1992, pp. 99–124, vol. 14, Plenum Press, USA.

Crute, I. and D. Pink, "Genetics and Utilization of Pathogen Resistance in Plants," *The Plant Cell*, Oct. 1996, pp. 1747–1755, vol. 8, American Society of Plant Physiologists.

Delledonne, M., et al., "Nitric Oxide Functions as a Signal in Plant Disease Resistance," *Nature*, Aug. 1998, pp. 585–588, vol. 394.

Durner, J., et al., "Defense Gene Induction in Tobacco by Nitric Oxide, Cyclic GMP, and Cyclic ADP–ribose," *Proc. Natl. Acad. Sci. USA*, Aug. 1998, pp. 10328–10333, vol. 95, The National Academy of Sciences.

Gopalan, S., et al., "Expression of the *Pseudomonas syringae* Avirulence Protein AvrB in Plant Cells Alleviates Its Dependence on the Hypersensitive Response and Pathogenicity (Hrp) Secretion System in Eliciting Genotype–Specific Hypersensitive Cell Death," *The Plant Cell*, Jul. 1996, pp. 1095–1105, vol. 8, American Society of Plant Physiologists.

Honee, G., et al., "Production of the AVR9 Elicitor From the Fungal Pathogen *Cladosporium fulvum* in Transgenic Tobacco and Tomato Plants," *Plant Molecular Biology*, 1995, pp. 909–920, vol. 29, Kluwer Academic Publishers, Belgium.

Leister, R., et al., "Molecular Recognition of Pathogen Attack Occurs Inside of Plant Cells in Plant Disease Resistance Specified by the *Arabidopsis* Genes RPS2 and RPM1," *Proc. Natl. Acad. Sci. USA*, Dec. 1996, pp. 15497–15502, vol. 93.

Parker, J., and M. Coleman, "Molecular Intimacy Between Proteins Specifying Plant–Pathogen Recognition," *TIBS*, Aug. 1997, pp. 291–296, vol. 22, Elsevier Science Ltd.

Scheffer, R., "Causes and Spread of Plant Disease," *The Nature of Disease in Plants*, 1997, pp. 9–14, Cambridge University Press, United Kingdom.

Scheffer, R., "How Pathogens Attack Plants," *The Nature of Disease in Plants*, pp. 15–34, Cambridge University Press, United Kingdom.

(List continued on next page.)

*Primary Examiner*—Elizabeth F. McElwain
*Assistant Examiner*—Medina A. Ibrahim
(74) *Attorney, Agent, or Firm*—Pioneer Hi-Bred International, Inc.

(57) ABSTRACT

Compositions and methods for enhancing disease resistance in plants are provided. The method involves transforming a plant with an avirulence gene or alternatively with an avirulence gene and the complementing resistance gene. A pathogen inducible promoter or alternatively a weak constitutive promoter is used to control the desired level of disease control in the plant. Transformed plants, plant cells, tissues, and seed are also provided having enhanced disease resistance.

10 Claims, 2 Drawing Sheets

OTHER PUBLICATIONS

Scheffer, R., "How Plants Defend against Pathogens," *The Nature of Disease in Plants*, 1997, pp. 35–41, Cambridge University Press, United Kingdom.

Scheffer, R., "Disease Controls and Their Limitations," *The Nature of Disease in Plants*, 1997, pp. 58–69, Cambridge University Press, United Kingdom.

Scofield, S., et al., "Molecular Basis of Gene–for–Gene Specificity in Bacterial Speck Disease of Tomato," *Science*, Dec. 20, 1996, pp. 2063–2065, vol. 274.

Sidler, M., et al., "Involvement of an ABC Transporter in a Developmental Pathway Regulating Hypocotyl Cell Elongation in the Light," *The Plant Cell*, Oct. 1998, pp. 1623–1636, vol. 10, American Society of Plant Physiologists.

Tang, X., et al., "Intiation of Plant Disease Resistance by Physical Interaction of AvrPto and Pto Kinase," *Science*, Dec. 20, 1996, pp. 2060–2063, vol. 274.

Whalen, M.C., et al., "Avirulence Gene avrRxv From *Xanthomonas capestris* pv. *vesicatoria* Specifies Resistance on Tomato Line Hawaii 7998," *Molecular Plant–Microbe Interactions*, 1993, pp. 616–627, vol. 6(5), The American Phytopathological Society.

* cited by examiner

METHODS FOR ENHANCING DISEASE RESISTANCE IN PLANTS

CROSS-REFERENCE

This application is a divisional of U.S. patent application Ser. No. 09/256,898, filed Feb. 24, 1999, now U.S. Pat. No. 6,476,292 which claims the benefit of U.S. Provisional Application Ser. No. 60/076,151, filed Feb. 26, 1998, and U.S. Provisional Application Ser. No. 60/092,464, filed Jul. 11, 1998, the contents of which are herein incorporated by reference in their entirety.

FIELD OF THE INVENTION

The invention relates to the genetic manipulation of plants, particularly to transforming plants with genes that enhance disease resistance.

BACKGROUND OF THE INVENTION

Disease in plants is caused by biotic and abiotic causes. Biotic causes include fungi, viruses, bacteria, and nematodes. Of these, fungi are the most frequent causative agent of disease on plants. Abiotic causes of disease in plants include extremes of temperature, water, oxygen, soil pH, plus nutrient-element deficiencies and imbalances, excess heavy metals, and air pollution.

A host of cellular processes enables plants to defend themselves from disease caused by pathogenic agents. These processes apparently form an integrated set of resistance mechanisms that is activated by initial infection and then limits further spread of the invading pathogenic microorganism.

Subsequent to recognition of a potentially pathogenic microbe, plants can activate an array of biochemical responses. Generally, the plant responds by inducing several local responses in the cells immediately surrounding the infection site. The most common resistance response observed in both nonhost and race-specific interactions is termed the "hypersensitive response" (HR). In the hypersensitive response, cells contacted by the pathogen, and often neighboring cells, rapidly collapse and dry in a necrotic fleck. Other responses include the deposition of callose, the physical thickening of cell walls by lignification, and the synthesis of various antibiotic small molecules and proteins. Genetic factors in both the host and the pathogen determine the specificity of these local responses, which can be very effective in limiting the spread of infection.

The hypersensitive response in many plant-pathogen interactions results from the expression of a resistance (R) gene in the plant and a corresponding avirulence (avr) gene in the pathogen. This interaction is associated with the rapid, localized cell death of the hypersensitive response. R genes that respond to specific bacterial, fungal, or viral pathogens, have been isolated from a variety of plant species and several appear to encode cytoplasmic proteins.

The resistance gene in the plant and the avirulence gene in the pathogen often conform to a gene-for-gene relationship. That is, resistance to a pathogen is only observed when the pathogen carries a specific avirulence gene and the plant carries a corresponding or complementing resistance gene. Because avrR gene-for-gene relationships are observed in many plant-pathogen systems and are accompanied by a characteristic set of defense responses, a common molecular mechanism underlying avrR gene-mediated resistance has been postulated. A simple model which has been proposed is that pathogen avr genes directly or indirectly generate a specific molecular signal (ligand) that is recognized by cognate receptors encoded by plant R genes.

Both plant resistance genes and corresponding pathogen avirulence genes have been cloned. The plant kingdom contains thousands of R genes with specific specificities for viral, bacterial, fungal, or nematode pathogens. Although there are differences in the defense responses induced during different plant-pathogen interactions, some common themes are apparent among R gene-mediated defenses. The function of a given R gene is dependent on the genotype of the pathogen. Plant pathogens produce a diversity of potential signals, and in a fashion analogous to the production of antigens by mammalian pathogens, some of these signals are detectable by some plants.

The avirulence gene causes the pathogen to produce a signal that triggers a strong defense response in a plant with the appropriate R gene. However, expressing an avirulence gene does not stop the pathogen from being virulent on hosts that lack the corresponding R gene. A single plant can have many R genes, and a pathogen can have many avr genes.

As noted, among the causative agents of infectious disease of crop plants, the phytopathogenic fungi play the dominant role. Phytopathogenic fungi cause devastating epidemics, as well as causing significant annual crop yield losses. All of the approximately 300,000 species of flowering plants are attacked by pathogenic fungi. However, a single plant species can be host to only a few fungal species, and similarly, most fungi usually have a limited host range.

Plant disease outbreaks have resulted in catastrophic crop failures that have triggered famines and caused major social change. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight. Accordingly, molecular methods are needed to supplement traditional breeding methods to protect plants from pathogen attack.

SUMMARY OF THE INVENTION

Compositions and methods for creating or enhancing resistance to plant pests are provided. The method involves stably transforming a plant with an avirulence gene operably linked with a promoter capable of driving expression of a gene in a plant cell. The avirulence gene product is capable of interacting with a complementing resistance gene in the plant. Where necessary, a plant can be stably transformed with both an avirulence gene and with the complementing resistance gene, both of which are operably linked with an appropriate promoter.

It is recognized that a variety of promoters will be useful in the invention the choice of which will depend in part upon the desired level of expression of the avirulence and/or the resistance genes in the plant, or alternatively, in the plant organ in which expression is desired. It is recognized that the levels of expression can be controlled to induce the disease resistance pathway resulting in levels of immunity in the plant or to induce cell death.

The methods of the invention find use in controlling plant pests, including fungal pathogens, viruses, nematodes, insects, and the like.

Transformed plants and seeds, as well as methods for making such plants and seeds are additionally provided.

DETAILED DESCRIPTION OF THE INVENTION

Figure 1:
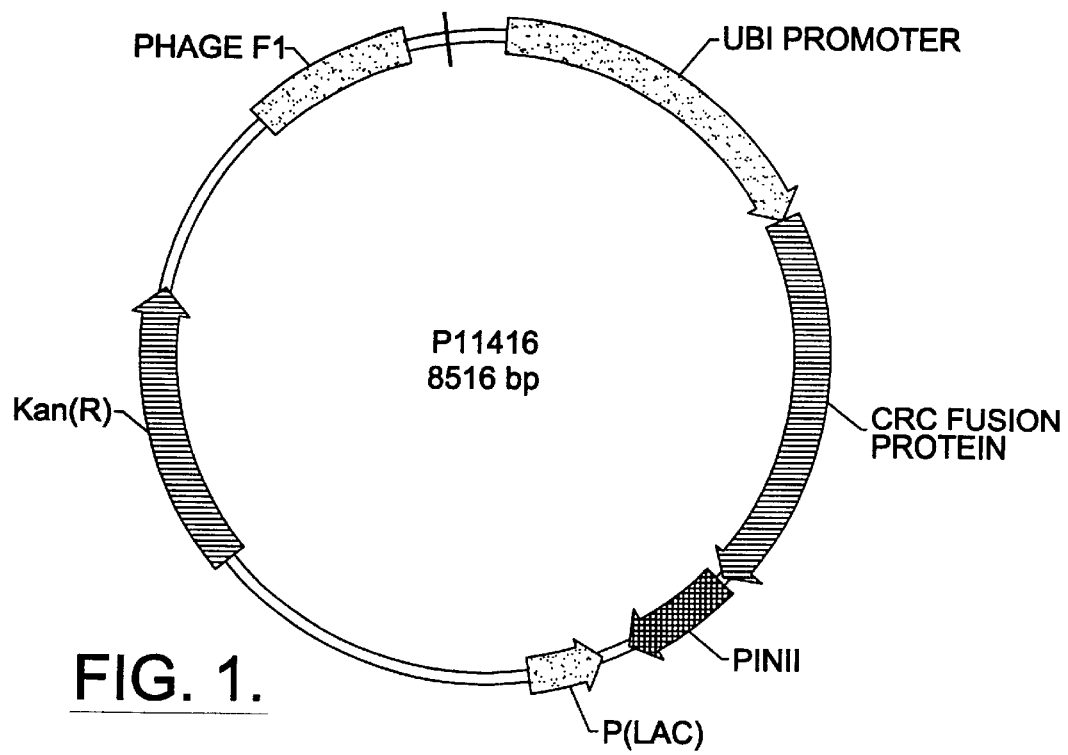
FIG. 1 schematically illustrates the plasmid construct comprising the ubiquitin promoter and CRC fusion protein gene.
Figure 2:
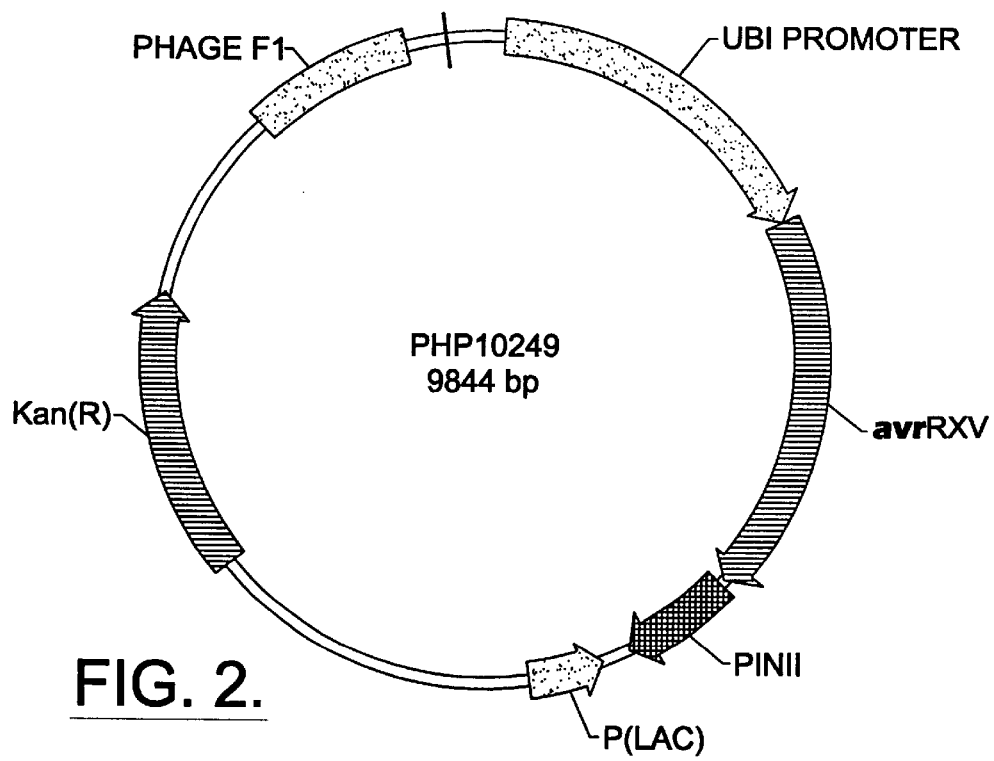
FIG. 2 schematically illustrates the plasmid construct comprising the ubiquitin promoter and AvrRxv gene.
Figure 3:
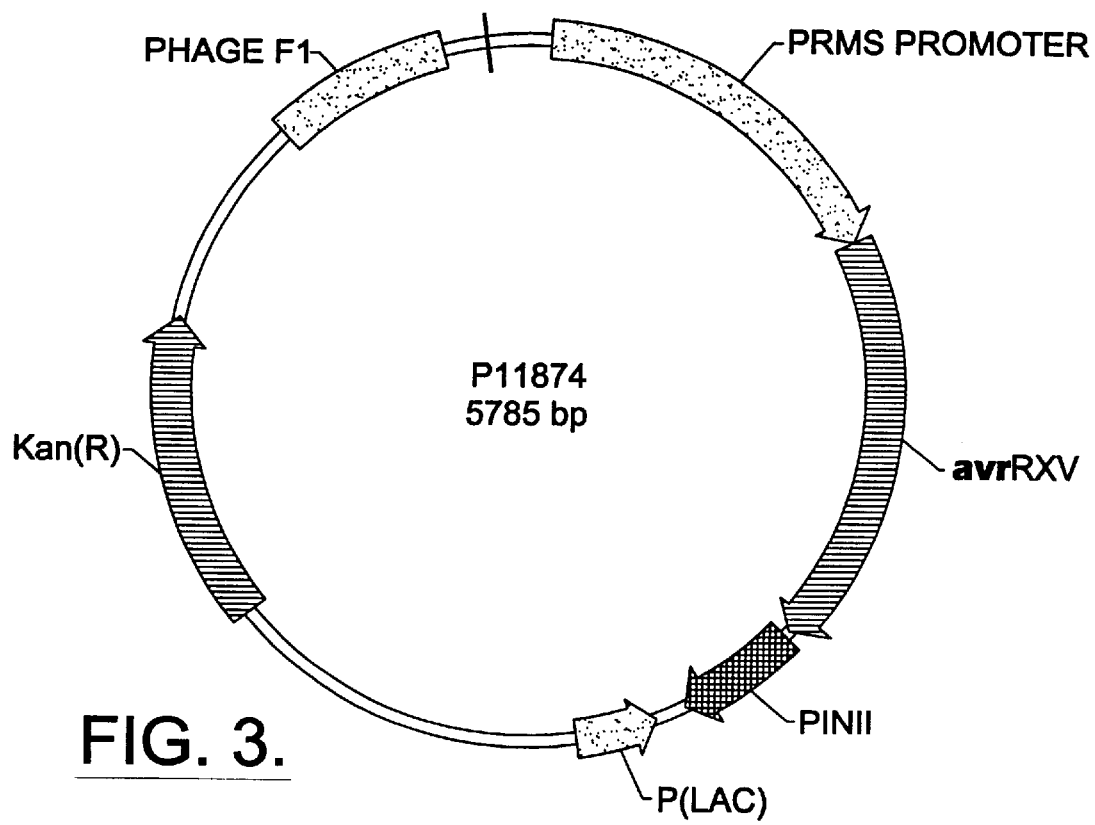
FIG. 3 schematically illustrates the plasmid construct comprising the PRms promoter and AvrRxv gene.

The invention is drawn to methods for creating or enhancing resistance in a plant to plant pests. Accordingly, the methods are also useful in protecting plants against fungal pathogens, viruses, nematodes, insects and the like.

By disease resistance is intended that the plants avoid the disease symptoms which are the outcome of plant-pathogen interactions. That is, pathogens are prevented from causing plant diseases and the associated disease symptoms. The methods of the invention can be utilized to protect plants from disease, particularly those diseases that are caused by plant pathogens.

Pathogens of the invention include, but are not limited to, viruses or viroids, bacteria, insects, nematodes, fungi, and the like. Viruses include tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthephaseolorum* var. *sojae (Phomopsis sojae), Diaporthephaseolorum var. caulivora, Sclerotium rolftsii, Cercospora kikuchii, Cercospora sojina, Peronospora manshurica, Colletotrichum dematium (Colletotichum truncatum), Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata, Soybean mosaic virus, Glomerella glycines*, Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium solani;* Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;* Alfalfa: *Clavibater michiganese subsp. insidiosum, Pythium ultimum, Pythium irregulare, Pythium splendens, Pythium debaryanum, Pythium aphanidermatum, Phytophthora megasperma, Peronospora trifoliorum, Phoma medicaginis var. medicaginis, Cercospora medicaginis, Pseudopeziza medicaginis, Leptotrochila medicaginis, Fusar-atrum, Xanthomonas campestris* p.v. *alfalfae, Aphanomyces euteiches, Stemphylium herbarum, Stemphylium alfalfae*; Wheat: *Pseudomonas syringae p.v. atrofaciens, Urocystis agropyri, Xanthomonas campestris* p.v. *translucens, Pseudomonas syringae p.v. syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminisfsp. tritici, Puccinia reconditafsp. tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis var. tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, Claviceps purpurea, *Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum pv. carotovora, Cephalosporium acremonium, Phytophthora cryptogea, Albugo tragopogonis;* Corn: *Fusarium moniliforme* zvar. *subglutinans, Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillusflavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatie-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, Claviceps sorghi, *Pseudonomas avenae, Erwinia chrysanthemi pv. zea, Erwinia corotovora, Cornstunt spiroplasma, Diplodia macrospora, Sclerophthora macrospora, Peronosclerospora sorghi, Peronosclerospora philippinensis, Peronosclerospora maydis, Peronosclerospora sacchari, Spacelotheca reiliana, Physopella zeae, Cephalosporium maydis, Caphalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternate, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root knot, cyst and lesion nematodes, etc.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus spp.*, wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus*, chinch bug; *Melanoplus femurrubrum*, redlegged grasshopper; *Melanoplus sanguinipes*, migratory grasshopper; *Hylemya platura*, seedcom maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus,* and *Aeolus spp.*, wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia ssp.*, Root maggots.

The methods of the invention rely upon the gene-for-gene interaction between avirulence and resistance genes. In plants, robust defense responses to invading pathogens often conform to a gene-for-gene relationship. Resistance to a pathogen is observed when the pathogen carries a specific avirulence (avr) gene and the plant carries a corresponding resistance (R) gene. Therefore, the methods of the invention involve transforming a plant with a specific avirulence gene. In those instances where the transformed plant contains a corresponding or complementing R gene, a hypersensitive response is induced when the avr and R genes are expressed. By "corresponding" or "complementing" is intended that the R gene is capable of recognizing and interacting with the particular avr gene product to invoke the hypersensitive response, or alternatively, to induce a level of immunity in the plant to minimize, reduce, and/or avoid pathogen infection.

The method relies upon the presence of a resistance (R) gene in the plant which is able to complement the avirulence gene. That is, for the HR to occur the R gene must recognize the gene product of the avirulence gene. Accordingly, a plant is transformed with an avirulence gene. Where the plant contains the complementing or corresponding R gene, a disease resistance reaction occurs. Where the plant does not contain a complementing R gene, methods are available for crossing into or transforming the plant with the appropriate R gene. Dominance of the appropriate R gene facilitates introduction of the gene by breeding methods. Then, expression of the two genes involves a hypersensitive reaction that includes cell death. The programmed cell death process in plant disease responses has definite characteristics such as DNA degradation. Additionally, it is involved in response to receptor-type R or resistance gene interactions. See, for example, Ryerson and Heath (1996) *Plant Cell* 8:393–402 and Dangl et al. (1996) *Plant Cell* 8:1793–1807.

Many of the plant resistance genes that are part of the gene-for-gene relationship mechanisms have been cloned. Many of the genes are leucine-rich repeat genes and/or protein kinases. See, for example, Cai et al. (1997) *Science* 275:832–834; and Roberts and Gallum (1984) *J. Heredity* 75:147–148. The expression of the two genes in the plant cell induces the disease resistance pathway or induces immunity in the plant. That is, the expression of the genes can induce a defense response in the cell or can turn on the disease resistance pathway to obtain cell death. The end result can be controlled by the level of expression of the avr gene in the plant. Where the expression is sufficient to cause cell death, such response is a receptor-mediated programmed response. See, for example, Ryerson and Heath (1996) *Plant Cell* 8:393–402 and Dangl et al. (1996) *Plant Cell* 8:1793–1807.

A number of promoters can be used in the practice of the invention. The promoters can be selected based on the desired outcome. When the genes are expressed at levels to cause cell death, an inducible promoter can be used to drive the expression of either the avr or both the avr and R genes. Where the R gene is present in the plant or is crossed into the plant through breeding methods, the avr gene can be expressed utilizing an inducible promoter. The inducible promoter generally needs to be tightly regulated to prevent unnecessary cell death yet be expressed in the presence of a pathogen to prevent infection and disease symptoms. Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *The Plant Cell* 4:645–656; and Van Loon (1985) *Plant Mol. Virol.* 4:111–116. See, also application Ser. Nos. 60/076,100 and 60/079,648 entitled "Inducible Maize Promoters," filed Feb. 26, 1998, and Mar. 27, 1998, respectively, and herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Molecular and General Genetics* 2:93–98; and Yang, Y (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; and the references cited therein. Of particular interest is the inducible promoter for the maize PRms gene, whose expression is induced by the pathogen *Fusarium moniliforme* (see, for example, Cordero et al. (1992) *Physiological and Molecular Plant Pathology* 41:189–200).

Additionally, as pathogens find entry into plants through wounds or insect damage, a wound inducible promoter may be used in the constructions of the invention. Such wound inducible promoters include potato proteinase inhibitor (pin II) gene (Ryan, C., *Annu Rev Phytopath* 28:425–449; Duan et al. *Nature Biotechnology* 14:494–498); wun1 and wun2, U.S. Pat. No. 5,428,148; win1 and win2 (Stanford et al. *Mol Gen Genet* 215:200–208); systemin (McGurl et al. *Science* 225:1570–1573); WIP1 (Rohmeier et al. *Plant Mol Biol* 22:783–792; Eckelkarnp et al. FEBS *Letters* 323:73–76); MPI gene (Corderok et al. *The Plant Journal* 6(2):141–150); and the like, herein incorporated by reference.

Where low level expression is desired to induce immunity but not cause cell death, weak promoters will be used. It is recognized that weak inducible promoters may also be used. Likewise, either a weak constitutive or a weak tissue specific promoter may be used. Such weak promoters cause activation of the plant defense system short of hypersensitive cell death. Thus, there is an activation of the plant defense system at levels sufficient to protect from pathogen invasion. In this state, there is at least a partial activation of the plant defense system wherein the plant produces increased levels of antipathogenic factors such as PR proteins, i.e., PR1, chitinases, β-glucanases, etc.; secondary metabolites; phytoalexins; reactive oxygen species; and the like.

Generally, by "weak promoter" is intended either a promoter that drives expression of a coding sequence at a low level. By "low level" is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 (copending application serial number 08/661,601), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; 5,608,142. See also, application Ser. No. 60/076,075 entitled "Constitution Maize Promoters" filed Feb. 26, 1998 and herein incorporated by reference.

Tissue specific promoters include Yamamoto et al. (1997) *Plant J.* 112(2):255–265; Kawamata et al. (1997) *Plant Cell Physiol.* 38(7):792–803; Hansen et al. (1997) *Mol Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol Biol.* 23(6):1129–1138; Matsuoka et al. (1993) *Proc. Natl. Acad. Sci. USA* 90(20):9586–9590; and Guevara-Garcia et al. (1993) *Plant J.* 4(3):495–505. Such promoters can be modified, if necessary, for weak expression.

A number of avirulence genes are known in the art and can be used in the invention. The avirulence gene will be chosen based upon the presence of a corresponding or complementing R gene in the plant to be transformed. Alternatively, where no corresponding R gene is present in the plant, it will be necessary to use an avirulence gene wherein the complementing or corresponding R gene is available to be cotransformed or crossed into the plant.

As noted above, the plant to be transformed with the avirulence gene will be tested for the presence of a complementing resistance gene. In those instances where no resistance gene is present, the resistance gene may be introduced by recombinant methods or alternatively by breeding.

For particular avirulence genes, see Puri et al. (1997) *Mol. Plant Microbe Interact.* 10(2):247–256; Gopalan et al. (1996) *Plant J.* 10(4):591–600; Gopalan et al. (1996) *Plant Cell* 8(7): 1095–1105; Ritter et al. (1995) *Mol. Plant Microbe Interact* 8(3):444–453; Yu et al. (1993) *Mol. Plant Microbe Interact.* 6(4):434–443; Dangl et al. (1992) *Plant Cell* 4(11):1359–1369; Dong et al. (1991) *Plant Cell* 3(1):61–72; Kearney et al. (1990) *Nature* 346(6282):385–386; Mansfield et al. (1994) *Mol. Plant Microbe Interact* 7(6):726–739; Tamaki et al. (1988) *J. Bacteriol.* 170(10):4846–4854; Yucel et al. (1994) *Mol. Plant Microbe Interact.* 7(5):677–679; Cournoyer et al. (1995) *Mol. Plant Microbe Interact.* 8(5):700–708; Tamaki et al. (1991) *J. Bacteriol* 173(1):301–307; Salmeron et al. (1993) *Mol. Gen. Genet.* 239(1–2):6–16; Ronald et al. (1992) J Bacteriol.

174(5):1604–1611; Alfano et al. (1996) *Mol. Microbiol.* 19(4):715–728; Wanner et al. (1993) *Mol. Plant Microbe Interact.* 6(5):582–591; Simonich et al. (1995) *Mol. Plant Microbe Interact.* 8(4):637–640; Lorang et al. (1995) *Mol. Plant Microbe Interact.* 8(1):49–57; Pirhonen et al. (1996) Mol. Plant Microbe Interact. 9(4):252–260; Hinsch et al. (1996) *Mol. Plant Microbe Interact.* 9(1):55–61; Shen et al. (1993) *J. Bacteriol.* 175(18):5916–5924; Heu et al. (1993) Mol. Plant Microbe Interact. 6(5):553–564; and Innes et al. (1993) *J. Bacteriol* 175(15):4859–4869; which disclosures are herein incorporated by reference.

In the same manner, resistance genes are known in the art. See, for example, Dixon et al. (1996) *Cell* 84(3):451–459; Reuber et al. (1996) *Plant Cell* 8(2):241–249; Grant et al. (1995) *Science* 269(5225):843–846; Bisgrove et al. (1994) *Plant Cell* 6(7):927–933; Dangl et al. (1992) *Plant Cell* 4(11):1359–1369; Ashfield et al. (1995) *Genetics* 141(4):1597–1604; Kunkel et al. (1993) *Plant Cell* 5(8):865–875; Reuber et al. (1996) *Plant Cell* 8(2):241–249; Grant et al. (1995) *Science* 269(5225):843–846; Dixon et al. (196) *Cell* 84(3):451–459; Jones et al. (1994) *Science* 266(5186):789–793; Mindrinos (1994) *Cell* 78(6):1089–1099; Bent et al. (1994) *Science* 265(5180):1856–1860; Dixon et al. (1995) *Mol. Plant Microbe Interact.* 8(2):200–206; Salmeron et al. (1996) *Cell* 86(1):123–133; Rommens et al. (1995) *Plant Cell* 7:1537–1544; Buschges et al. (1997) *Cell* 88(5):695–705; Dixon et al. (1996) *Cell* 84:451–459; Song et al. (1995) *Science* 270(5243):1804–1806; Grant et al. (1995) *Science* 269(5225):843–846; Rommens et al. (1995) *Plant Cell* 7(10):1537–1544; Loh et al. (1995) *Proc. Natl. Acad. Sci. USA* 92(10):4181–4184; Tomero et al. (1996) *Plant J.* 10(2):315–330; Staskawicz et al. (1995) *Science* 268(5211):661–667; Whitham et al. (1994) *Cell* 78(6):1101–1115; Dickinson et al. (1993) *Mol. Plant Microbe Interact.* 6(3):341–347; Innes et al. (1993) *Plant J.* 4:813–820; Reuber et al. (1996) *Plant Cell* 8(2):241–249; Kunkel et al. (1993) *Plant Cell* 5(8):865–875; Leister et al. (1996) *Proc. Natl. Acad. Sci. USA* 93(26):15497–15502; Bisgrove et al. (1994) *Plant Cell* 6(7):927–933; Dangl et al. (1992) *Plant Cell* 4(11):1359–1369; Kanazin et al. (1996) *Proc. Natl. Acad. Sci. USA* 93(21):11746–11750; Hammond-Kosack et al. (1996) *Plant Cell* 8(10):1773–1791; and Buschges et al. (1997) *Cell* 88(5):695–705; which disclosures are herein incorporated by reference.

To determine whether the plant to be transformed contains within its genome the corresponding R gene to a particular avr gene, the avirulence gene can be introduced into the plant in a transgenic experiment. The avirulence gene is introduced into the plant, along with a reporter gene. Constitutive promoters will be used to drive both the avirulence gene and the reporter gene or genes. If there is a functional resistance gene corresponding to the avirulence gene in the plant, then the cells that have been transformed will die, resulting in little or no expression of the reporter gene. In other words, the presence of a complementing R gene and avr gene will result in a hypersensitive response in the plant, resulting in cell death. This death will preclude the expression of the reporter gene.

Reporter genes are available in the art. Reporter genes should ideally exhibit low background activity and should not have any detrimental effects on metabolism. The reporter gene products will have moderate stability in vivo, so that down-regulation of gene expression as well as gene activity can be detected. Finally, the reporter gene should be able to be assayed by a quantitative, sensitive, simple to perform and inexpensive system.

Reporter genes are known in the art and include but are not limited to:

Beta-glucuronidase (GUS) gene (Jefferson et al. (1991) *In Plant Molecular Biology Manual* (Gelvin et al., eds.), pp. 1–33, Kluwer Academic Publishers). This gene is encoded by the uidA locus of *E. coli*. GUS enzyme activity can be assayed easily and sensitively in plants. The expression of GUS gene fusions can be quantified by fluorometric assay, and histochemical analysis can be used to localize gene activity in transgenic tissues. Luciferase (DeWet et al. (1987) *Mol. Cell. Biol.* 7:725–737). Luciferase catalyzes the oxidation of D(—)-luciferin in the presence of ATP to generate oxyluciferin and yellow-green light.

Anthocyanins (Goff et al. (1990) *EMBO J.* 9:2517–2522). Anthocyanin is a reporter system that does not require the application of external substrates for its detection. The anthocyanin system utilizes the C1, Bz and R genes, which code for transacting factors that regulate the anthocyanin biosynthetic pathway in maize seeds. The introduction of these regulatory genes under the control of constitutive promoters includes cell-autonomous pigmentation in non-seed tissues.

Green fluorescent protein (GFP) from the jellyfish *Aequorea Victoria* (Kain et al. (1995) *BioTechniques,* 19:650–655 and Chiu et al. (1996) *Current Biology,* 6:325–330). GFP emits bright green light when excited with UV or blue light. GFP fluorescence does not require a substrate or cofactor, is stable, and can be monitored non-invasively in living cells.

The avirulence and/or R genes of the invention can be introduced into any plant. The genes to be introduced will be used in expression cassettes for expression in any plant of interest.

Such expression cassettes will comprise a transcriptional initiation region linked to the gene encoding the R or avr gene of interest. Such an expression cassette is provided with a plurality of restriction sites for insertion of the gene of interest to be under the transcriptional regulation of the regulatory regions. The expression cassette may additionally contain selectable marker genes.

The transcriptional initiation region, the promoter, may be native or analogous or foreign or heterologous to the plant host. Additionally, the promoter may be the natural sequence or alternatively a synthetic sequence. By foreign is intended that the transcriptional initiation region is not found in the native plant into which the transcriptional initiation region is introduced. As used herein a chimeric gene comprises a coding sequence operably linked to a transcription initiation region that is heterologous to the coding sequence. For purposes of the screen to determine if the plant contains a complementary R gene, any promoter or promoter element capable of driving expression of a coding sequence can be utilized, of particular interest are constitutive promoters (See, for example, U.S. Pat. Nos. 5,608,149; 5,608,144; 5,604,121; 5,569,597; 5,466,785; 5,399,680; 5,268,463; 5,608,142), herein incorporated by reference. As discussed above, when both the R and avr genes are being introduced into a plant only one of the genes will need to be controlled by an inducible promoter, the other gene can be regulated by a constitutive promoter.

The transcriptional cassette will include in the 5'–3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens,* such as the octopine synthase and nopaline synthase termination regions. See also, Guerineau et al., (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nuc. Acids Res.* 17:7891–7903; Joshi et al. (1987) *Nuc. Acid Res.* 15:9627–9639.

The genes of the invention are provided in expression cassettes for expression in the plant of interest. The cassette will include 5' and 3' regulatory sequences operably linked to the gene of interest. The cassette may additionally contain at least one additional gene to be cotransformed into the organism. Alternatively, the additional gene(s) can be provided on another expression cassette. Where appropriate, the gene(s) may be optimized for increased expression in the transformed plant. That is, the genes can be synthesized using plant preferred codons for improved expression. Methods are available in the art for synthesizing plant preferred genes. See, for example, U.S. Pat. Nos. 5,380,831, 5,436, 391, and Murray et al. (1989) *Nuc. Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picomavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak and Samow (1991) Nature 353:90–94; untranslated leader from the coat protein mRNA of alfalfa mosaic virus (AMV RNA 4), (Jobling and Gehrke (1987) *Nature* 325:622–625; tobacco mosaic virus leader (TMV), (Gallie et al. (1989) *Molecular Biology of RNA*, pages 237–256; and maize chlorotic mottle virus leader (MCMV) (Lommel et al. (1991) *Virology* 81:382–385). See also, Della-Cioppa et al. (1987) *Plant Physiology* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions, may be involved.

The genes of the present invention can be used to transform any plant. In this manner, genetically modified plants, plant cells, plant tissue, seed, and the like can be obtained. Transformation protocols may vary depending on the type of plant or plant cell, i.e. monocot or dicot, targeted for transformation. Suitable methods of transforming plant cells include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055), direct gene transfer (Paszkowski et al. (1984) *EMBO J* 3:2717–2722), and biolistic particle acceleration (see, for example, Sanford et al., U.S. Pat. No. 4,945,050; Tomes et al., "Direct DNA Transfer into Intact Plant Cells via Microprojectile Bombardment," In Gamborg and Phillips (Eds.) *Plant Cell, Tissue and Organ Culture: Fundamental Methods*, Springer-Verlag, Berlin (1995); and McCabe et al. (1988) *Biotechnology* 6:923–926). Also see, Weissinger et al. (1988) *Annual Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) Bio/Technology 6:923–926 (soybean); Datta et al. (1990) *Bio-technology* 8:736–740 (rice); Klein et al. (1988) *Proc. Natl. Acad. Sci. USA* 85:4305–4309 (maize); Klein et al. (1988) *Biotechnology* 6:559–563 (maize); Tomes et al. "Direct DNA Transfer into Intact Plant Cells via Microprojectile Bombardment" In Gamborg and Phillips (Eds.) *Plant Cell, Tissue and Organ Culture:* Fundamental Methods, Springer-Verlag, Berlin (1995); Tomes, U.S. Pat. No. 5,240,855; Buising et al. U.S. Pat. Nos. 5,322,783 and 5,324, 646 (maize); Klein et al. (1988) *Plant Physiol.* 91:440–444 (maize); Fromm et al. (1990) *Biotechnology* 8:833–839 (maize); Hooydaas-Van Slogteren & Hooykaas (1984) *Nature* (London) 311:763–764; Bytebier et al. (1987) *Proc. Natl. Acad. Sci. USA* 84:5345–5349 (Liliaceae); De Wet et al. (1985) In *The Experimental Manipulation of Ovule Tissues, ed. Chapman et al., pp.* 197–209, Longman, N.Y. (pollen); Kaeppler et al. (1990) *Plant Cell Reports* 9:415–418; and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells which have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The methods of the present invention provide an improvement over the previous approach of matching avirulence and resistance genes via traditional breeding methods. After the demonstration that disease resistance can be conferred by single genes, breeders of many crops initiated breeding programs with the expectation that the resulting control of plant diseases would be permanent. Durable disease resistance based on the utilization of one or more single dominant R genes has been achieved in some cases. More frequently, however, the rapid evolution of matching pathotypes virulent on previously resistant cultivars has forced breeders into a repetitive cycle of cultivar replacement demanding the continual introgression of new resistance specialties.

In contrast, the present method relies upon an inducible promoter which is turned on in the presence of the pathogen and is not necessarily dependent upon the recognition of a ligand or protein produced by the pathogen. Alternatively, weak constitutive promoters are likely to induce a level of immunity in the plant. Accordingly, there may be no increased selection pressure against the matching avr allele in the pathogen population. Therefore, single mutational events at the corresponding avr locus may not result in a new virulent pathotype.

Importantly, while methods have suggested the use of avr genes to transform plants, there has been no demonstration that the methods would result in disease resistant plants until the present work. In fact, most of the previous work has dealt with establishing the gene-for-gene relationship in dicotyledonous plants. There have been no reports of the transformation and expression of an avr gene in a monocotyledonous plant. Furthermore, none of the work to date would have suggested that a pathogen avr gene which induces the HR in a particular dicot could be used to elicit the response in a monocot.

The methods of the invention can be used with other methods available in the art for enhancing disease resistance in plants.

The following examples are offered by way of illustration and not by way of limitation.

EXPERIMENTAL

EXAMPLE 1

Disease Resistant Transient Gene Expression Assay Using Biolistics Particle Bombardment A transient gene expression assay, as modified from Nelson and Bushnell (*Transgenic Res. (*1997) 6:233–244), was used to evaluate the ability of an introduced avirulence gene, whose expression product would induce expression of an unknown resident resistance gene in a host plant cell, to confer a hypersensitive response within the host cell. In the method, a particle bombardment system was used to simultaneously introduce a construct comprising a reporter gene driven by a constitutive promoter and a construct comprising an avirulence gene with its promoter into maize cells for the purposes of studying physiological processes, foremost amongst them the plant defense response.

In this example, the first construct comprised a ubiquitin promoter driving the expression of the reporter CRC fusion protein gene, which when expressed causes cells to turn red due to anthocyanin production. Other reporter genes, such as GUS, luciferase, or green fluorescent protein, can be used in this assay. The second construct comprised the AvrRxv gene driven by the constitutive ubiquitin promoter. This gene, the nucleotide sequence of which is published (Whalen et al. (1993) *Mol. Plant Microb. Interact.* 6:616–627; Accession No. L20423), is from *Xanthomonas campestris pv vesicatoria,* a pathogen of tomato. Expression of the AvrRxv gene product causes interaction of that gene product with a resident maize resistance gene, termed Rxv, if such a gene is present. Following cobombardment of cells with these constructs, expression of the AvrRxv gene and Rxv protein interact within a cell causing a hypersensitive-type disease response involving cell death, or at the very least radically redirected gene expression. Such cell death disrupts the expression of the reporter gene, such that the occurrence of visible, anthocyanin-containing phenotypes is suppressed in these cobombardment experiments.

Tissue sources.

Experiments were performed with immature embryos, essentially the scutellar surface. Mature embryos from germinated seeds have also been used with similar results.

Immature embryos from an inbred line are isolated from ears 9–11 days after pollination using a scalpel. Prior to embryo isolation, pollinated ears are surface-sterilized with a microdetergent and 25% commercial bleach mixture, and washed with 3 exchanges of sterile H2O. The embryos are transferred to a high sucrose culture medium and aligned in a target grid about 1.4 cm wide for bombardment.

DNA Sources.

The DNA constructs of interest used in this example included: plasmid p11416 (FIG. 1), comprising the ubiquitin promoter (ubi) and the CRC fusion protein gene (ubi::CRC fusion), the expression of which yields the anthocyanin-producing, or red cell, phenotype; and plasmid p10249 (FIG. 2), comprising the ubiquitin promoter and the AvrRxv gene (ubi::AvrRxv), the expression of which yields the AvrRxv product. Plasmid p7770 (not shown), comprising an empty ubiquitin promoter construct (ubi::pinll terminator), was used as a control to balance promoter site molarity; and plasmid p7731 (not shown), an inert DNA filler, was used to balance the amount of DNA shot with each bombardment episode.

Embryos were transformed by the tungsten particle biolistic method (Tomes et al. (1995) supra; Koziel et al. (1993) *Bio/Technology* 11:194–200) using a high pressure particle delivery system (Biolistic Particle Delivery System Model PDS-100 by DuPont). Forty-five embryos, arranged in 5 plates, each with 9 embryos, were subjected to bombardment with the ubi::CRC fusion construct alone (Treatment A) or to cobombardment with the ubi::CRC fusion construct and the ubi::AvrRxv construct (Treatment B). Following bombardment, embryos were stored in the dark for 36 hours at 23° C.

Quantification and Verification of Gene Expression.

Expression of the CRC fusion gene was quantified by visual means 16 to 48 hours, more usually 36 hours, following bombardment. Cells expressing the CRC fusion protein gene are red in color. The number of red cells on all 9 embryos within each plate was counted and an average number of spots calculated for the 45 embryos bombarded with the ubi::CRC fusion construct (Treatment A) and the 45 embryos bombarded with the ubi::CRC fusion and ubi::AvrRxv construct (Treatment B).

Activation of the defense system, using the maize PR1 protein as a marker, was verified with an antibody Western blot for the PR1 class of pathogenesis-related proteins. Forty-eight hours after bombardment, 18 embryos for each treatment were pooled and their protein extracted and run on SDS-PAGE, electroblotted onto 0.2 micron PVDV membrane, and probed with antibodies raised against tobacco PR1 protein.

Interpretation of Results.

Expression of the CRC fusion protein gene alone (Treatment A) yielded a high number of expressing events or red spots. Expression of the CRC fusion protein gene was suppressed when the AvrRxv gene was expressed (Treatment B), yielding a much reduced number of expressing events or red spots (FIG. 3). This suppression of reporter gene expression suggests the presence of an Rxv gene within the maize embryos, whose expression is identified in the presence of the AvrRxv gene product, such that a defense response is triggered, disrupting anthocyanin. Support for such a conclusion is provided in several other studies that similar transient expression may approach (Gopalan et al.

(1996) *Plant Cell* 8:1095–1105; Leister et al. (1996) *Proc. Natl. Acad. Sci. USA* 93:15497–15502; Scofield et al. (1996) *Science* 274:2063–2065; and Tang et al. (1996) *Science* 274:2060–2062). In these studies, plant cells containing a known resistance gene and cotransformed with a known avirulence gene construct, both under the regulation of a constitutive promoter, exhibited suppression of reporter gene expression and stimulation of a necrotic defense response.

Table 1 sets forth the expression of CRC anthocyanin reported gene system in particle bombarded maize tissues with or without cobombardment with the AvrRxv gene. The Table demonstrates that there is genotype dependence of suppression of CRC expression indicating the presence or absence of a functional cognate resistance gene, Rxv. It is noted that about two-thirds of the inbreds tested have the Rxv gene.

The results also demonstrate that the Rxv gene is dominant, or at least, semi-dominant. This is indicated by the effect being observed in the hybrid 3394, which is the progeny of PHN46 (Rxv positive) and PHP38 (Rxv negative).

The magnitude of the AvrRxv::Rxv effect on reporter gene expression varies for different experiments on the same inbred as well as between inbreds and tissues, indicating a difference in Rxv allelic strength or differences in Rxv expression. Likewise, inherent experimental variation may account for some of the expression variation.

Expression of the AvrRxv gene sequences in maize tissue causes elevated expression of defense-related markers, such as PR1 protein. The elevated PRI protein expression was observed in two types of bombarded tissues, immature embryos and leaves, indicating the likely widespread developmental expression of Rxv, and hence widespread competency of the maize plant to respond to AvrRxv in a defense-related manner.

TABLE 1

Expression of CRC anthocyanin reporter gene system in particle bombarded maize tissues with or without cobombardment with the AvrRxv gene: Genotype dependence of AvrRxv suppression of CRC expression.

| Maize Line | Tissue[1] | CRC Control Ave[4] | SE[4] | CRC + AvrRxv Ave[4] | SE[4] | Ratio[2] | Rxv[3] |
|---|---|---|---|---|---|---|---|
| PHN46 | ME | 27 | 10 | 0.3 | 0.5 | 90.0 | + |
| PHN46 | ME | 349 | 142 | 8 | 9 | 43.6 | + |
| PHN46 | ME | 467 | 103 | 94 | 22 | 5.0 | + |
| PHN46 | ME | 57 | 75 | 2 | 2 | 28.5 | + |
| PHN46 | ME | 184 | 145 | 4 | 3 | 46.0 | + |
| PHN46 | IM[5] | 188 | 48 | 46 | 16 | 4.1 | + |
| PHN46[6] | IM | 188 | 48 | 4 | 1 | 47.0 | + |
| B73 | LF | 41 | 11 | 21 | 5 | 2.0 | + |
| B73 | LF | 9 | 2 | 1.3 | 0.5 | 6.9 | + |
| B73 | LF[5] | 51 | 17 | 23 | 6 | 2.2 | + |
| B73 | LF | 286 | 48 | 177 | 26 | 1.6 | + |
| 1047 | ME | 51 | 36 | 14 | 5 | 3.6 | + |
| B73 | ME | 99 | 113 | 2 | 2 | 49.5 | + |
| PHKM0 | ME | 14 | 10 | 0.3 | 0.6 | 46.7 | + |
| CN3K7 | ME | 114 | 93 | 0.7 | 1.2 | 162.9 | + |
| PH428 | ME | 186 | 200 | 42 | 37 | 4.4 | + |
| PHHB9 | ME | 178 | 274 | 44 | 29 | 4.0 | + |
| 953 | ME | 142 | 23 | 14 | 14 | 10.1 | + |
| PHP02 | ME | 80 | 23 | 40 | 35 | 2.0 | + |
| PHN82 | ME | 120 | 115 | 7 | 6 | 17.1 | + |
| PHK03 | ME | 94 | 51 | 34 | 45 | 2.8 | + |
| 3394[7] | ME | 81 | 87 | 25 | 23 | 3.2 | + |
| PHK76 | ME | 19 | 10 | 23 | 11 | 0.8 | − |
| PHKE1 | ME | 134 | 108 | 97 | 41 | 1.4 | − |
| PHW52 | ME | 81 | 21 | 88 | 76 | 0.9 | − |

TABLE 1-continued

Expression of CRC anthocyanin reporter gene system in particle bombarded maize tissues with or without cobombardment with the AvrRxv gene: Genotype dependence of AvrRxv suppression of CRC expression.

| Maize Line | Tissue[1] | CRC Control Ave[4] | SE[4] | CRC + AvrRxv Ave[4] | SE[4] | Ratio[2] | Rxv[3] |
|---|---|---|---|---|---|---|---|
| PHW52 | ME | 113 | 59 | 105 | 47 | 1.1 | − |
| PHP38 | ME | 114 | 89 | 146 | 111 | 0.8 | − |
| PHK46 | ME | 19 | 26 | 17 | 14 | 1.1 | − |
| PH647 | ME | 29 | 24 | 49 | 42 | 0.6 | − |
| PHK56 | ME | 228 | 163 | 248 | 184 | 0.9 | − |
| M017 | ME | 119 | 41 | 165 | 71 | 0.7 | −[1] |

[1]Tissues are: ME, mature embryo; IE, immature embryo; and LF, leaf.
[2]Ratio of average number of red transformed spots (cells) for CRC control over average number for CRC + AvrRxv.
[3]When the CRC/CRC + AvrRxv ratio exceeds 2, Rxv is generally concluded present (+); when less than 2, Rxv is concluded absent (−).
[4]Averages and standard errors from N = 3 separate bombardments for mature embryos, N = 5 for immature embryos, and between N = 8 to 10 for leaves.
[5]Immature embryo and leaf tissue bombardments used for PR westerns.
[6]Here AvrRxv gene DNA amount 10-fold higher than other experiments.
[7]3394 is a hybrid of PHN46 × PHP38.

Immature embryos cobombarded with the ubi::CRC fusion construct and the ubi::AvrRxv construct exhibit elevated PR1 expression relative to embryos bombarded with the ubi::CRC fusion construct alone, or embryos not bombarded. It is striking that so large an effect was observed given the relatively small numbers of transformed cells in the embryos. This elevated PR1 expression indicates activation of the defense system in the embryos transformed with the AvrRxv construct. Elevated expression of PR1 protein was detected on western blots. Activation of this well-known defense-related gene is one indication that a hypersensitive response is likely to have occurred.

Numerous other adaptations of this approach using different genes and promoters could address a number of issues relating to plant defense and other physiological processes. For example, instead of using AvrRxv to cause a defense reaction, we could use any other gene that may be suspected to cause a disease response (for example, from an EST collection) and bombard it in along with the reporter gene to determine whether there is a defense reaction. One could also tribombard using the reporter gene, the AvrRxv, and a gene that is presumed to block the defense pathway. In this case, expression of the reporter gene would not be expected to be suppressed.

EXAMPLE 2

Use of a Pathogen Inducible Promoter and the AvrRxv Gene to Enhance the Pathogen Defense Response System One way by which the avrR gene may be used to develop an enhanced pathogen defense response system is to have the AvrRxv coding region driven by a promoter that is inducible by pathogen attack. Following identification of genes that are induced by exposure to the pathogen *Fusarium moniliforme*, the inducible promoters for these genes are cloned using a "gene-walker" system. This system basically involves primer extension using a primer site on the 5' end of the cDNA.

Several such promoters are cloned and linked to the AvrRxv coding regions for testing in both transient assays and stable transformed plants.

The PRms gene and promoter.

The first such promoter to have been cloned next to the AvrRxv gene is that of the PRms gene. This is a maize gene that is induced by *Fusarium moniliforme* treatment. It also has some developmental expression apart from pathogen treatment. The PRms gene is related to the PR1 class of pathogenesis-related proteins, a class first identified and characterized in tobacco. The PRms expression pattern has been published (see, for example, Cordero et al. (1992) *Physiological and Molecular Plant Pathology* 41:189–200; Casacuberta et al. (1992) *Molecular and General Genetics* 234:97–104; and Murillo et al. (1997) *The Plant Cell* 9:145–156), and the PRms promoter has been sequenced (Raventos et al. (1995) *Plant J.* 7(1):147–155; Accession No. X78337).

PRms promoter in transient assays.

A plasmid construct comprising the PRms promoter::AvrRxv coding region has been tested in the transient assay system described in Example 1 using mature embryo scutellum of the maize inbred line in Example 1. It was observed that the PRms::AvrRxv construct did not cause a suppression of the CRC anthocyanin-producing reporter system. This appears to indicate that the basal or background expression of the AvrRxv gene with the PRms promoter does not produce enough AvrRxv product to elicit the AvrRxv-Rxv defense response. This being the case, finding an inducible promoter to drive AvrRxv expression may not require an especially low basal (i.e., not pathogen induced) level of expression to avoid triggering the AvrRxv-Rxv defense response.

These transformed embryos are exposed to the *Fusarium moniliforme* pathogen, or an elicitor from the pathogen. A decrease in expression of the CRC reporter gene, as evidenced by decreased number of red cells, indicates a defense response has occurred.

PRms Promoter in Stable Transformants.

The PRms::AvrRxv construct described for transient assays is used to create stable maize transformants. Following bombardment and selection of maize embryos, stably transformed plants are produced. (Tomes et al. "Direct DNA transfer into intact plant cells via microprojectile bombardment" In Gamborg and Phillips (Eds.) Plant Cell, Tissue and Organ Culture: Fundamental Methods, Springer-Verlag, Berlin (1995). Healthy stable transformants indicate that the basal level and developmental expression from the PRms promoter does not induce death by precipitating the AvrRxv-Rxv defense response. Such plants are used to determine whether localized exposure to the *Fusarium moniliforme* pathogen elicits a pathogen-induced hypersensitive or death response, as evidenced by localized lesions or cell death resulting in containment of the pathogen in the areas of initial contact. Such a response indicates the inducible PRms promoter is functional in AvrRxv stably transformed plants.

Other Pathogen Inducible Promoters.

Other pathogen inducible promoters, such as the maize PR1 promoter, are isolated, characterized, and linked to the AvrRxv coding region for testing similar to that described for the PRms promoter. The transient system is used to identify promoters that have low-level background expression before proceeding with production of stable transformants.

EXAMPLE 3
Use of a Constitutive Promoter and the AvrRxv Gene to Enhance the Pathogen Defense Response System in Leaf Tissue The avrR gene or other avirulent gene may be used to develop a pathogen defense response system in particular plant tissues. In this manner the AvrRxv coding region is driven by a constitutive promoter. The ubi::AvrRxv construct was cobombarded with CRC into maize leaf tissue. Protocols for the transformations was as described above. The leaf tissue was isolated from L6–L7 plants grown in the greenhouse for approximately 3 weeks. The tender nearly white leaves wrapped at the center of the whorl were isolated, unfurled and laid on the agar bombing medium. After bombardment the tissue was incubated for 48 hours in the dark and red spots were counted. The results demonstrated a suppression of the CRC expression relative to controls. A 2–3 fold suppression was observed demonstrating that the strategy works in various tissues and against various diseases.

EXAMPLE 4
AvrRxv Defense-Inducing System in Stable Transformed Maize Tissue

Transgenic maize callus/cell lines expressing the AvrRxv gene under the direction of the ERE (estrogen response element) promoter construct were regenerated. The ERE promoter construct is an estrogen inducible gene expression system. The results indicate that induced AvrRxv expression causes the activation of maize pathogen defense systems. ERE-AvrRxv callus treated with estradiol were subjected to mRNA profiling. A set of induced gene expression changes were identified. These induced genes are largely genes whose expression is known or suspected to be involved in pathogen defense.

EXAMPLE 5
ERE-AvrRxv mRNA Profiling Experiment

The purpose of the experiment was to profile gene expression changes associated with the induced expression of AvrRxv, and to determine whether these gene expression changes are consistent with activation of the plant (cells) defense system. The callus line used for this experiment previously showed elevated expression of PR1, chitinase, and cationic peroxidases following induction with estradiol. Additionally, the line showed browning and accumulation of phenolics.

Materials and Methods Transgenic maize callus transformed with the ERE-AvrRxv construct was used. This callus is from line "197" and was the same used in earlier experiments described above. Similar GS3 callus transformed with a construct containing only the selectable marker gene, but not the ERE-AvrRxv chimeric gene, was used as control. The callus from these two backgrounds was divided into two samples. These samples were plated on fresh agar selection medium. For the induction with estradiol, one plate for each genotype was treated with estradiol in an aqueous/ethanolic solution. The other plate for each genotype served as a non-induced control and received aqueous/ethanolic solution without estradiol. This application was time 0. These plates were then left open in the dark overnight in a flow hood to dry. On day three (T+72 hours), the applications and flow hood drying was repeated. On day five (T+120 hours) the tissue was harvested and frozen in liquid nitrogen. Frozen tissue was ground with a mortar and pestle and its mRNA was extracted by the trizol method (Molecular Research Center, Inc). PolyA mRNA was isolated. PolyA was converted to cDNA, and then to cRNA labeled with fluorescent tags. This in vitro transcript (IVT) was hybridized to chips. These chips contained (usually) twenty 25-mer oligonucleotides matching each of hundreds of maize cDNAs (ESTs). In addition twenty related oligonucleotides for each cDNA were used. Hybridization, image detection, data normalization, and algorithmic analysis were conducted. Relative fold change in hybridizing intensity was compared between estradiol-treated versus control samples for both the ERE-AvrRxv genotype and the GS3 genotype. The results indicate those genes (cDNAs) that have changed (here induced) expression of at least two-fold in the ERE-AvrRxv callus treated with estradiol relative to the GS3 callus treated with estradiol represent a set of genes that is defense related. In fact, nearly all, if not all, of the genes are known or suspected to be defense related.

Discussion This mRNA profiling data demonstrated that the AvrRxv gene, when induced using the Estradiol/ERE promoter system, causes the activation of maize defense systems. The nature of the set of induced genes is clearly defense-related. Few if any non defense-related genes are induced, further indicating that the AvrRxv activation is specific for defense.

EXAMPLE 6
AvrRxv Timecourse Northern Experiment

The purpose of this experiment was two-fold. The first is to show that the AvrRxv gene mRNA expression is indeed induced in ERE-AvrRxv callus treated with estradiol. The second is to obtain a time course of its induced and to relate that to the rate of induction of defense-related factors.

Materials and Methods Suspension cultures transformed with the ERE::AvrRxv construct were treated with estradiol in an aqueous/ethanolic solution. Cells were harvested at the follow time points: 0, 6, 12, 24, or 48 hours. Total RNA was isolated and 30 ug per lane were run on a denaturing agarose gel. The gel was blotted on to a nylon backed nitro-cellulose membrane and subsequently hybridized with a DNA probe containing the AvrRxv open reading frame.

Results The results indicated that induction of the AvrRxv transcript by treatment with estradiol occurs in as little as 1 hour, is strongly induced in 4 hrs., and continues until 48 hrs. Without estradiol treatment very little AvrRxv transcript is made.

Discussion The induced expression of AvrRxv expression by 6 hours following estradiol treatment indicates that the response is fairly rapid. More importantly, this response at the MRNA level is more rapid than the activation of the defense system, at least earlier than the overt characteristics such as browning and growth stunting.

EXAMPLE 7
PCR and Southern Determination of the Presence of the AvrRxv Gene in Transgenic Maize Callus Lines The purpose of this experiment was to determine whether the callus purported to be transgenic with the ERE-AvrRxv construct does indeed contain that construct as revealed by Southern blots and PCR tests.

Materials and Methods Standard Southern blot technology was followed using purified genomic DNA from callus followed by restriction enzyme digestion, gel electrophoresis, blotting to a membrane, and probing with a portion of the AvrRxv gene. In addition, standard PCR detection of the AvrRxv gene was observed using primers specific to the AvrRxv gene.

Results The callus line was used in many of these ERE-AvrRxv experiments was PCR positive for AvrRxv and by Southern blot the gene was detected.

Discussion The data indicated that the callus line was indeed transformed with the ERE-AvrRxv construct. The northern data for AvrRxv gene expression was also positive. The induction of expression following estradiol treatment demonstrated that the construct was transcriptionally inducible by elicitor.

In summary, both in transient bombardments of maize tissue, and in stable promoter-inducible maize callus lines, AvrRxv is behaving as an activator of the defense response.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for creating or enhancing disease resistance in a monocotyledonous plant to Fusarium, said method comprising transforming said plant with an expression cassette comprising the coding sequence of the AvrRxv avirulence gene operably linked to a promoter, wherein said promoter is selected from the group consisting of the core promoter of the Rsyn7 promoter and the core promoter of the 35S CaMV promoter, and regenerating stably transformed plants with enhanced disease resistance to Fusarium.

2. The method of claim 1, wherein said promoter is the core promoter of the Rsyn7 promoter.

3. A monocot plant stably transformed with a DNA construct comprising the coding sequence of the AvrRxv avirulence gene operably linked to a promoter, wherein said promoter is selected from the group consisting of the core promoter of the Rsyn7 promoter and the core promoter of the 35S CaMV promoter.

4. The plant of claim 3, wherein said monocot is maize.

5. The plant of claim 4, wherein said promoter is the core promoter of the Rsyn7 promoter.

6. Seed of the plant of claim 3 wherein said seed comprises said DNA construct.

7. Seed of the plant of claim 4 wherein said seed comprises said DNA construct.

8. Seed of the plant of claim 5 wherein said seed comprises said DNA construct.

9. A monocot plant cell comprising in its genome a DNA construct comprising the coding sequence of the AvrRxv avirulence gene operably linked to a promoter, wherein said promoter is selected from the group consisting of the core promoter of the Rsyn7 promoter and the core promoter of the 35S CaMV promoter.

10. The plant cell of claim 9, wherein said promoter is the core promoter of the Rsyn7 promoter.

* * * * *